United States Patent
Gill et al.

(10) Patent No.: US 12,178,974 B2
(45) Date of Patent: Dec. 31, 2024

(54) GUIDEWIRE AND METHOD OF USE

(71) Applicant: Abbott Cardiovascular Systems Inc., Santa Clara, CA (US)

(72) Inventors: Puneet Kamal Singh Gill, Anaheim, CA (US); Jonathan P. Durcan, Temecula, CA (US); Matthew Vasquez, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 740 days.

(21) Appl. No.: 17/154,938

(22) Filed: Jan. 21, 2021

(65) Prior Publication Data

US 2022/0226617 A1 Jul. 21, 2022

(51) Int. Cl.
*A61M 25/09* (2006.01)
*A61L 31/08* (2006.01)
*A61L 31/14* (2006.01)

(52) U.S. Cl.
CPC ............ *A61M 25/09* (2013.01); *A61L 31/088* (2013.01); *A61L 31/14* (2013.01); *A61L 2420/02* (2013.01); *A61M 2025/09075* (2013.01); *A61M 2025/09108* (2013.01); *A61M 2025/09141* (2013.01); *A61M 2025/09158* (2013.01)

(58) Field of Classification Search
CPC ........ A61M 25/09; A61M 2025/09058; A61M 2025/09075; A61M 2025/09108; A61M 2025/09133; A61M 25/01; A61M 2025/09
See application file for complete search history.

(56) References Cited

U.S. PATENT DOCUMENTS

| | | |
|---|---|---|
| 4,538,622 A | 9/1985 | Samson et al. |
| 4,748,986 A | 6/1988 | Morrison et al. |
| 4,818,486 A | 4/1989 | Rothman et al. |
| 4,875,489 A | 10/1989 | Messner et al. |
| 4,917,104 A | 4/1990 | Rebell |
| 4,925,445 A | 5/1990 | Sakamoto et al. |
| 4,955,384 A | 9/1990 | Taylor et al. |
| 4,964,926 A | 10/1990 | Hill |
| 4,966,163 A | 10/1990 | Kraus et al. |
| 5,061,273 A | 10/1991 | Yock |
| 5,069,217 A | 12/1991 | Fleischhacker |
| 5,069,226 A | 12/1991 | Yamauchi et al. |
| 5,135,503 A | 8/1992 | Abrams |
| 5,171,383 A | 12/1992 | Sagae et al. |
| 5,213,111 A | 5/1993 | Cook et al. |
| 5,230,348 A | 7/1993 | Ishibe et al. |

(Continued)

FOREIGN PATENT DOCUMENTS

WO 0032265 A1 6/2000

OTHER PUBLICATIONS

International Search Report, Mar. 28, 2022, 2 pages, from counterpart application PCT/US2022/011786.

*Primary Examiner* — Eric F Winakur
*Assistant Examiner* — Abel Seifu Abegaz
(74) *Attorney, Agent, or Firm* — Fulwider Patton LLP

(57) ABSTRACT

A guidewire formed from drawn filled tubing having an inner core member encased in an outer layer. The inner core member is formed from a linear elastic or superelastic material and the outer layer is formed from a metal alloy such as 35N LT. A portion of the outer layer is ground down to form a feather edged joint between the outer layer and the inner core member.

62 Claims, 8 Drawing Sheets

(56) References Cited

U.S. PATENT DOCUMENTS

| | | | |
|---|---|---|---|
| 5,238,004 A | 8/1993 | Sahatjian et al. | |
| 5,253,653 A | 10/1993 | Daigle et al. | |
| 5,341,818 A | 8/1994 | Abrams et al. | |
| 5,345,945 A | 9/1994 | Hodgson et al. | |
| 5,365,943 A | 11/1994 | Jansen | |
| 5,402,799 A * | 4/1995 | Colon | A61M 25/09033 |
| | | | 600/585 |
| 5,411,476 A | 5/1995 | Abrams et al. | |
| 5,506,059 A | 4/1996 | Robbins et al. | |
| 5,520,194 A | 5/1996 | Miyata et al. | |
| 5,588,443 A | 12/1996 | Davidson | |
| 5,607,463 A | 3/1997 | Schwartz et al. | |
| 5,628,787 A | 5/1997 | Mayer | |
| 5,630,840 A | 5/1997 | Mayer | |
| 5,636,641 A | 6/1997 | Fariabi | |
| 5,636,642 A | 6/1997 | Palermo | |
| 5,637,089 A | 6/1997 | Abrams et al. | |
| 5,647,858 A | 7/1997 | Davidson | |
| 5,664,580 A | 9/1997 | Erickson et al. | |
| 5,695,111 A | 12/1997 | Nanis et al. | |
| 5,720,300 A | 2/1998 | Fagan et al. | |
| 5,725,570 A | 3/1998 | Heath | |
| 5,725,572 A | 3/1998 | Lam et al. | |
| 5,733,326 A | 3/1998 | Tomonto et al. | |
| 5,749,837 A | 5/1998 | Palermo et al. | |
| 5,776,080 A | 7/1998 | Thome et al. | |
| 5,824,056 A | 10/1998 | Rosenberg | |
| 5,824,077 A | 10/1998 | Mayer | |
| 5,827,201 A | 10/1998 | Samson et al. | |
| 5,843,166 A | 12/1998 | Lentz et al. | |
| 5,885,381 A | 3/1999 | Mitose et al. | |
| 5,891,191 A | 4/1999 | Stinson | |
| 5,916,166 A | 6/1999 | Reiss et al. | |
| 5,951,793 A | 9/1999 | Mitose et al. | |
| 5,984,878 A | 11/1999 | Engelson | |
| 6,019,736 A | 2/2000 | Avellanet et al. | |
| 6,068,623 A | 5/2000 | Zadno-Azizi et al. | |
| 6,132,389 A | 10/2000 | Cornish et al. | |
| 6,142,975 A | 11/2000 | Jalisi et al. | |
| 6,200,685 B1 | 3/2001 | Davidson | |
| 6,217,567 B1 | 4/2001 | Zadno-Azizi et al. | |
| 6,245,030 B1 | 6/2001 | DuBois et al. | |
| 6,296,616 B1 | 10/2001 | McMahon | |
| 6,340,441 B1 | 1/2002 | Meyer et al. | |
| 6,352,515 B1 | 3/2002 | Anderson et al. | |
| 6,432,066 B1 | 8/2002 | Ferrera | |
| 6,488,637 B1 | 12/2002 | Eder et al. | |
| 6,579,246 B2 | 6/2003 | Jacobsen et al. | |
| 6,610,155 B2 | 8/2003 | Pike et al. | |
| 6,855,161 B2 | 2/2005 | Boylan et al. | |
| 7,632,237 B2 | 12/2009 | Murayama et al. | |
| 7,645,242 B1 | 1/2010 | Jalisi et al. | |
| 7,670,526 B2 | 3/2010 | Solar et al. | |
| 7,722,551 B2 | 5/2010 | Murayama et al. | |
| 7,785,274 B2 | 8/2010 | Mishima et al. | |
| 7,922,673 B2 | 4/2011 | Murayama et al. | |
| 7,993,286 B2 | 8/2011 | Reynolds et al. | |
| 7,998,090 B2 | 8/2011 | Simpson et al. | |
| 8,007,447 B2 | 8/2011 | Murayama et al. | |
| 8,057,405 B2 | 11/2011 | Jalisi et al. | |
| 8,083,689 B2 | 12/2011 | Vrba | |
| 8,109,887 B2 | 2/2012 | Murayama et al. | |
| 8,109,888 B2 | 2/2012 | Terashi et al. | |
| 8,137,291 B2 | 3/2012 | Melsheimer | |
| 8,192,373 B2 | 6/2012 | Sakane et al. | |
| 8,226,577 B2 | 7/2012 | Jalisi et al. | |
| 8,257,278 B2 | 9/2012 | Howland et al. | |
| 8,262,588 B2 | 9/2012 | Miyata et al. | |
| 8,262,589 B2 | 9/2012 | Lupton | |
| 8,308,658 B2 | 11/2012 | Albers et al. | |
| 8,313,445 B2 | 11/2012 | Mishima et al. | |
| 8,348,859 B2 | 1/2013 | Murayama et al. | |
| 8,348,860 B2 | 1/2013 | Murayama et al. | |
| 8,353,849 B2 | 1/2013 | Tamai et al. | |
| 8,353,850 B2 | 1/2013 | Ressemann et al. | |
| 8,360,996 B2 | 1/2013 | Satou et al. | |
| 8,403,867 B2 | 3/2013 | Nowak, Jr. | |
| 8,414,506 B2 | 4/2013 | Reynolds et al. | |
| 8,500,658 B2 | 8/2013 | Boyle et al. | |
| 8,517,959 B2 | 8/2013 | Kurosawa et al. | |
| 8,574,170 B2 | 11/2013 | Eskuri | |
| 8,585,612 B2 | 11/2013 | Nishigishi | |
| 8,585,613 B2 | 11/2013 | Nagano et al. | |
| 8,652,119 B2 | 2/2014 | Nishigishi | |
| 8,679,035 B2 | 3/2014 | Boyle et al. | |
| 8,708,932 B2 | 4/2014 | Tamai et al. | |
| 8,740,814 B2 | 6/2014 | Koike | |
| 8,740,815 B2 | 6/2014 | Palme, Jr. et al. | |
| 8,758,269 B2 | 6/2014 | Miyata et al. | |
| 8,795,202 B2 | 8/2014 | Northrop et al. | |
| 8,827,926 B2 | 9/2014 | Kinoshita et al. | |
| 8,827,928 B2 | 9/2014 | Nabeshima et al. | |
| 8,852,126 B2 | 10/2014 | Miyata et al. | |
| 8,858,468 B2 | 10/2014 | Sela et al. | |
| 8,905,946 B2 | 12/2014 | Boyle et al. | |
| 8,939,916 B2 | 1/2015 | Jacobsen et al. | |
| 8,945,024 B2 | 2/2015 | Takata et al. | |
| 8,956,310 B2 | 2/2015 | Miyata et al. | |
| 8,961,434 B2 | 2/2015 | Miyata et al. | |
| 8,961,435 B2 | 2/2015 | DeMello | |
| 8,968,215 B2 | 3/2015 | Murayama et al. | |
| 8,968,216 B2 | 3/2015 | Terashi et al. | |
| 8,986,224 B2 | 3/2015 | Echarri | |
| 8,986,225 B2 | 3/2015 | Folk | |
| 9,005,138 B2 | 4/2015 | Urbanski et al. | |
| 9,017,268 B2 | 4/2015 | Miyata et al. | |
| 9,028,427 B2 | 5/2015 | Kinoshita et al. | |
| 9,028,428 B2 | 5/2015 | Maki | |
| 9,033,004 B2 | 5/2015 | Mishima et al. | |
| 2003/0229298 A1* | 12/2003 | Iwami | A61M 25/09 |
| | | | 600/585 |
| 2005/0049523 A1* | 3/2005 | Crank | A61M 25/09 |
| | | | 600/585 |
| 2006/0122537 A1* | 6/2006 | Reynolds | A61L 31/022 |
| | | | 600/585 |
| 2007/0083132 A1* | 4/2007 | Sharrow | A61M 25/0012 |
| | | | 600/431 |
| 2009/0131913 A1* | 5/2009 | Grandfield | A61M 25/09 |
| | | | 604/528 |
| 2016/0067456 A1* | 3/2016 | Burkett | A61B 5/6852 |
| | | | 600/486 |
| 2016/0135827 A1* | 5/2016 | Elsesser | A61F 2/962 |
| | | | 606/159 |
| 2018/0311477 A1 | 11/2018 | Telang | |

\* cited by examiner

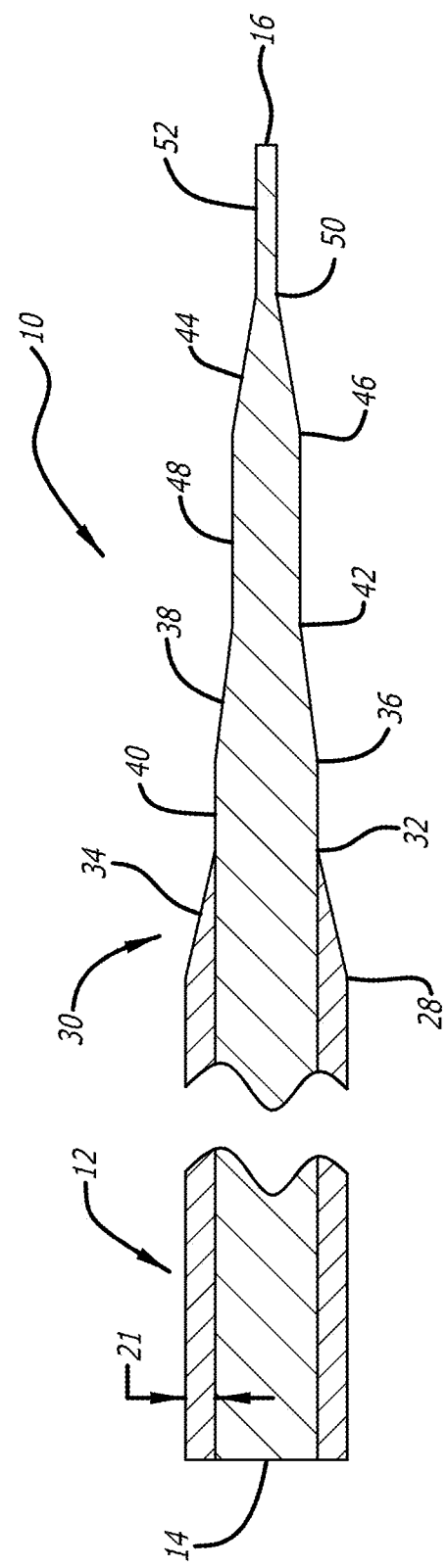
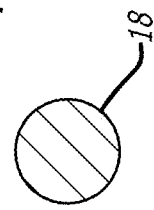
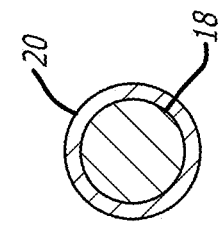

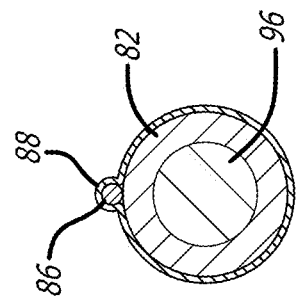
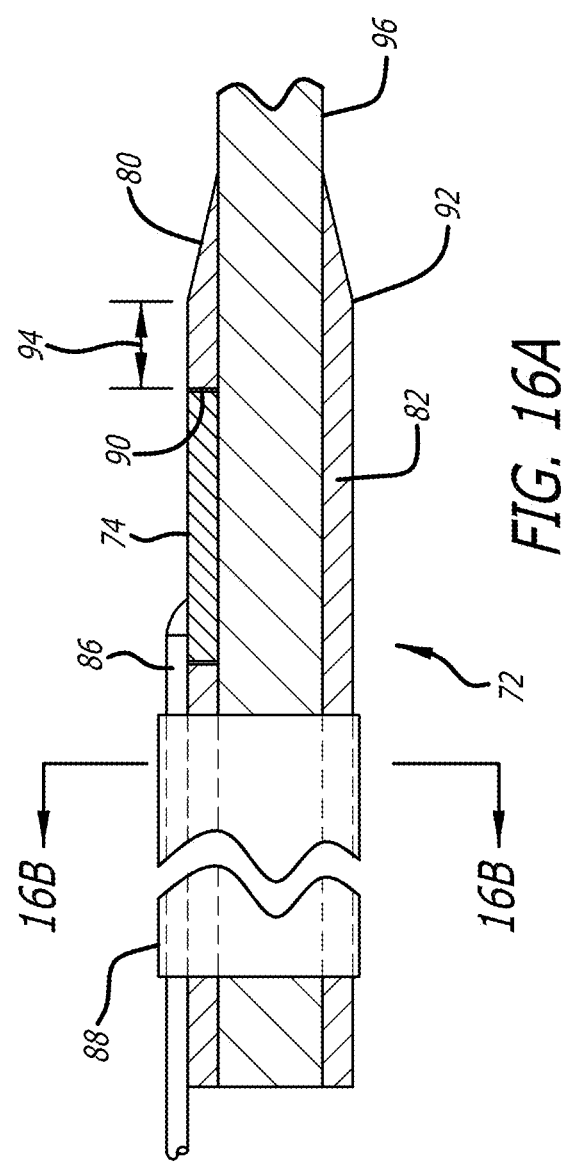

GUIDEWIRE AND METHOD OF USE

BACKGROUND

Conventional guidewires for angioplasty and other vascular procedures usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded tip at the distal end of the flexible body.

In a typical coronary procedure, a guidewire having a preformed distal tip is percutaneously introduced into a patient's peripheral artery, e.g., the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the procedure is performed.

A requirement for guidewires is that they have sufficient column strength to be pushed through a patient's vascular system or other body lumen without kinking. However, guidewires must also be flexible enough to avoid damaging the blood vessel or other body lumen through which they are advanced. Efforts have been made to improve both the strength and flexibility of guidewires to make them more suitable for their intended uses, but these two properties are for the most part, diametrically opposed to one another in that an increase in one usually involves a decrease in the other.

Some guidewires have been formed from a superelastic alloy such as a nitinol (nickel-titanium or NiTi) alloy, to achieve both flexibility and strength. When stress is applied to nitinol alloy exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation.

If the load on the specimen is removed before any permanent deformation has occurred, the martensitic phase of the specimen will elastically recover and transform back to the austenite phase. The reduction in stress first causes a decrease in strain. As stress reduction reaches the level at which the martensite phase transforms back into the austenite phase, the stress level in the specimen will remain essentially constant until the transformation back to the austenite phase is complete, i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity. These properties to a large degree allow a guidewire core of a superelastic material to have both flexibility and strength.

While the properties of the guidewire formed of the superelastic material were very advantageous, it was found that the guidewires and guiding members formed of materials having superelastic characteristics did not have optimum push and torque characteristics.

As is known in the art, many materials used for guidewire construction have desirable mechanical properties, but are difficult to assemble to other guidewire components using conventional technology such as soldering or use of polymer adhesives due to inherent surface properties such as tenacious oxide layers. In one prior art guidewire, a nitinol wire is joined to the proximal end of a stainless steel wire by either a hypotube/glue arrangement, or dissimilar weld. This joint typically has an abrupt stiffens transition from the nitinol to the stainless steel, has complex manufacturing steps, and is expensive to manufacture.

The present invention allows for the design of a guidewire with a unitary core, rather than a core with proximal and distal segments joined together. Additionally, the core member of the present invention may be used with other wire designs to create guidewires with improved superelasticity and kink-resistance.

SUMMARY OF THE INVENTION

It is an important aspect of the guidewire disclosed herein to utilize the structural features of a metal alloy having high yield strength for pushability and torque performance combined with a metal alloy having a high degree of elasticity for flexibility and trackability performance.

In one embodiment, an elongated tubular member has a proximal end and a distal end and includes an inner core member and an outer layer over the inner core member. The inner core member is formed from a first metal alloy and the outer layer is formed from a second metal alloy that is different than the first metal alloy. A feather edged joint defining a tapered transition segment is formed between the outer layer and the inner core member. Preferably a section of the outer layer is ground down to form the feather edged joint. The tapered transition segment extends from a first point on the outer layer where the nominal transverse wall thickness is constant, to a second point where the nominal transverse wall thickness of the outer layer is zero. In other words, the tapered segment extends between the first point where the wall thickness of the outer layer is thickest and then tapers (from the grinding process) to the second point where the wall thickness of the outer layer has been ground down to zero and the inner core member is exposed. In this embodiment, the inner core member is further ground at certain points along its length to form multiple tapered sections along a distal segment of the inner core member. Importantly, no portion of the outer layer surrounds the inner core member distal of the second point.

In one embodiment, a drawn filled tube has a proximal end and a distal end and includes an inner core member and an outer layer over the inner core member. The inner core member is formed from a first metal alloy and the outer layer is formed from a second metal alloy that is different than the first metal alloy. A feather edged joint defining a tapered transition segment is formed between the outer layer and the inner core member. Preferably a section of the outer layer is ground down to form the feather edged joint. The tapered transition segment extends from a first point on the outer layer where the nominal transverse wall thickness is constant, to a second point where the nominal transverse wall thickness of the outer layer is zero. In other words, the tapered segment extends between the first point where the wall thickness of the outer layer is thickest and tapered (from the grinding process) to the second point where the wall thickness of the outer layer has been ground down to zero and the inner core member is exposed. In this embodiment, the inner core member is ground at certain points along its length to form multiple tapered sections along a distal segment of the inner core member. Importantly, no portion of the outer layer surrounds the inner core member distal of the second point.

In one embodiment, the drawn filled tubing guidewire has a parabolic grind at a distal section thereof to take advantage of the nitinol inner core member.

In another embodiment, a pressure sensor is attached to a sensor pocket formed in a proximal section of a drawn filled tubing guidewire.

BRIEF DESCRIPTION OF THE DRAWINGS

FIG. 4 is a transverse cross-sectional view of the guidewire of FIG. 3 taken along line 4-4.

FIG. 5 is a transverse cross-sectional view of the guidewire of FIG. 3 taken along line 5-5.

FIG. 6 is a longitudinal cross-sectional view of the guidewire depicting the feather edged joint and multiple distal section tapers.

FIG. 16A is a longitudinal cross-sectional view of the guidewire shown in FIG. 15 depicting a polymer sleeve covering the power and data cable.

FIG. 16B is a transverse cross-sectional view taken along lines 16B-16B depicting the polymer sleeve covering the power and data cable.

DETAILED DESCRIPTION OF THE PREFERRED EMBODIMENTS

Figure 1:
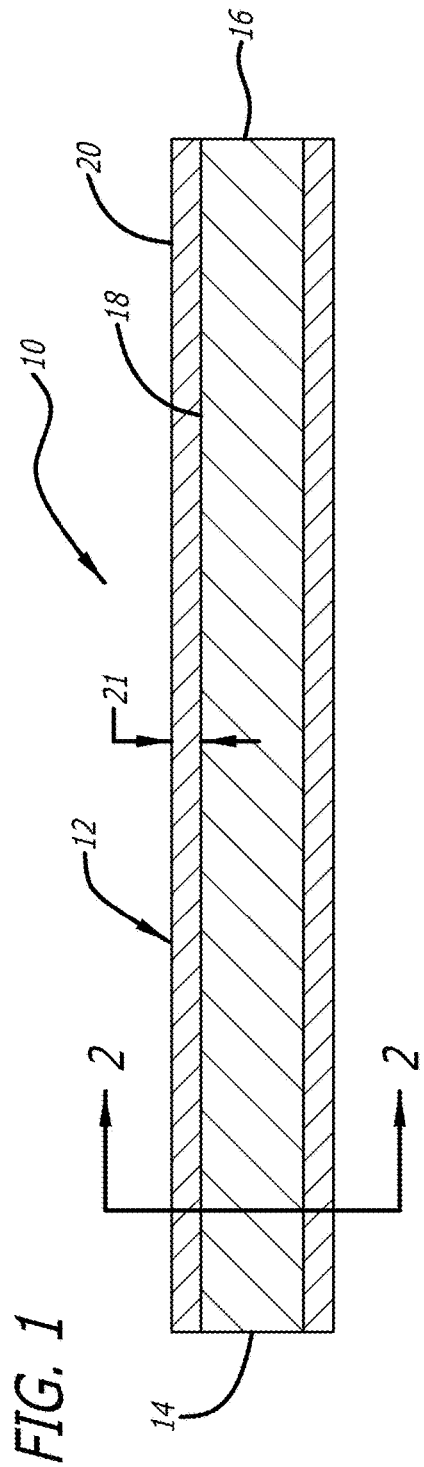
FIG. 1 is a longitudinal cross-sectional view of a guidewire depicting an outer layer surrounding an inner core member.
Figure 2:
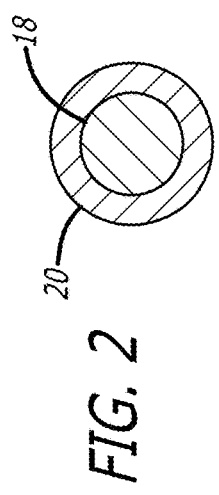
FIG. 2 is a transverse cross-sectional view of the guidewire of FIG. 1 taken along line 2-2.
Figure 3:
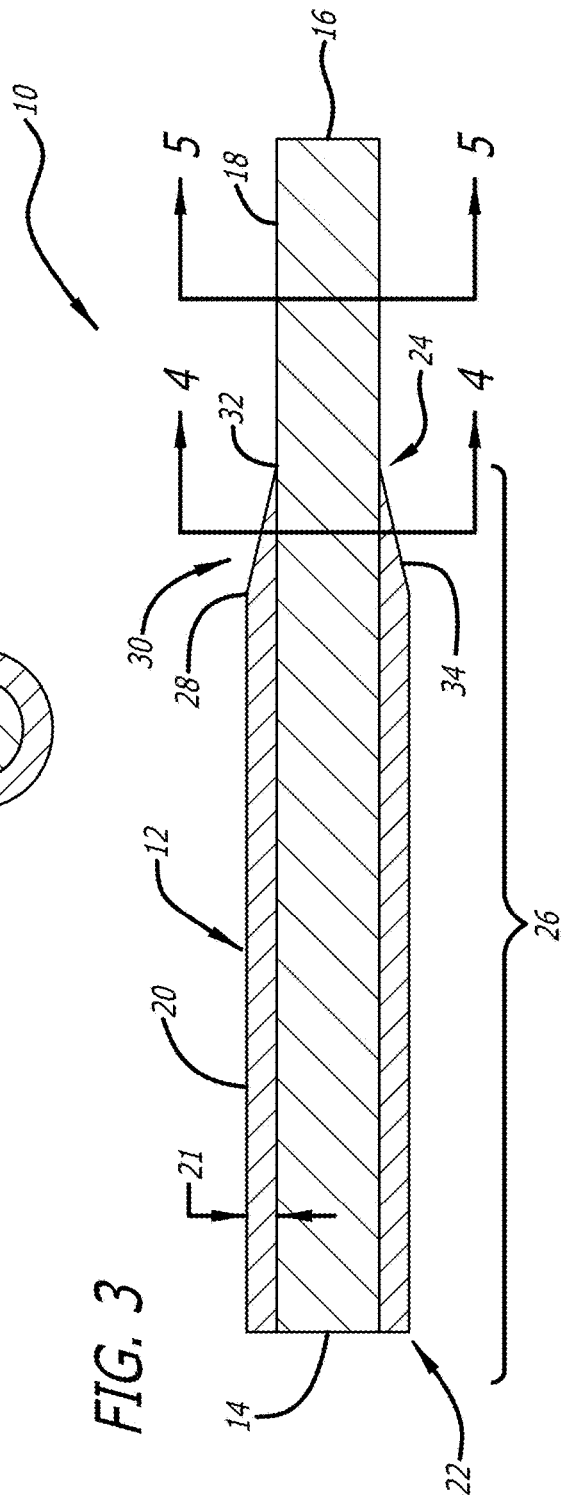
FIG. 3 is a longitudinal cross-sectional view of the guidewire of FIG. 1 depicting a feather edged joint.

FIGS. 1-6 illustrate features of a guidewire 10 embodying features of the invention. A composite elongated tubular member 12 has a proximal end 14 and a distal end 16. The elongated tubular member has an inner core member 18 that extends from the proximal end 14 to the distal end 16 and preferably is a solid core wire formed from a linear elastic alloy or a superelastic alloy. An outer layer 20 covers or surrounds the inner core member 18 along elongated tubular member 12. A wall thickness 21 of the outer layer 20 is shown in FIGS. 1, 3 and 6 and is sometimes referred to herein as a single wall thickness 21. The outer layer 20 is formed from a precipitation hardenable material such as 35N LT, stainless steel, L605, MP35, MP35N, cobalt chromium, titanium, NiTiCo, NiTiCr, NiTi ternary alloys and similar metal alloys. More specifically, the outer layer 20 extends from the proximal end 14 in a distal direction to the distal end 16. It is preferred that the outer layer 20 tightly surrounds the inner core member 18 with no space or gaps between the structures. The inner core member 18 is preferably formed from linear elastic or superelastic alloys and can include NiTi, CuNiTi, NiTiCr, NiTiCo, and similar metal alloys. The elongated tubular member 12 is typically drawn filled tubing (DFT) that is commercially available from several sources such as Fort Wayne Metals, Fort Wayne, Indiana.

In one embodiment, shown in FIGS. 1-6, a portion of the outer layer 20 is ground down to expose the inner core member 18. The outer layer has a proximal end 22 and a distal end 24 and a proximal segment 26 that extends from the proximal end 22 to a first point 28 that is closer to the distal end 24 than the proximal end 22. In this embodiment, a feather edged joint 30 is formed by grinding down the outer layer 20 from the first point 28 to a second point 32. The outer layer 20 is ground down so that the feather edged joint 30 forms a tapered transition segment 34 that gradually tapers from the first point 28 to the second point 32. The tapered transition segment 34 of the feather edged joint 30 extends a length along the elongated tubular member 12 beginning at the first point 28 where the nominal transverse wall thickness of the outer layer 20 is a constant, and ends at the second point 32 where the nominal transverse wall thickness of the outer layer 20 is zero. The length of the tapered transition segment 34 extends from first point 28 to the second point 32 and preferably is in the range of 0.079 inch (2.0 mm) to 1.000 inch (25.4 mm). Importantly, one critical aspect of the invention is to form a joint between two dissimilar metals such as 35N LT (the outer layer 20) and linear elastic or superelastic nitinol (the inner core member 18), which traditionally is difficult or impossible to achieve by welding, brazing, or the like. The feather edged joint 30 provides a seamless transition between the two metals thereby significantly improving the structural aspects of the joint as well as enhancing the tactile feel for the physician. In this embodiment, the inner core member 18 is further ground down to form multiple distal tapers to enhance flexibility in the distal portion of the guidewire. Starting at the second point 32 on the inner core member 18 and moving distally to a third point 36, the inner core member 18 has a first constant diameter section 40. Starting at the third point 36 and moving distally to a fourth point 42, the inner core member 18 is ground down to form a first tapered section 38. The inner core member 18 has a second constant diameter section 48 extending from the fourth point 42 to a fifth point 46. The inner core member 18 is ground down to form a second tapered section 44 extending from the fifth point 46 to a sixth point 50. The inner core member 18 has a third constant diameter section 52 that extends from the sixth point 52 to the distal end 16 of the elongated tubular member 12. Importantly, the nitinol distal portion of the guidewire having multiple tapers allows the guidewire to maneuver through tortuous anatomy without permanent deformation of the guidewire.

The overall length and diameter of guidewire 10 may be varied to suit the particular procedures in which it is to be used and is dependent on the materials from which it is constructed. Generally, the length of the guidewire 10 ranges from about 65 cm to about 350 cm, and more typically ranging from about 160 cm to about 200 cm. In one embodiment, the guidewire 10 is 180 cm long.

Commercially available guidewires for coronary and peripheral anatomy typically have lengths of about 175 cm or about 330 cm. Guidewire diameters generally range from about 0.008 inch to about 0.035 inch (0.2 to 0.9 mm), and more typically range from about 0.01 inch to about 0.018 inch (0.25 to 0.55 mm). Commercially available guide wires for coronary and peripheral use typically have diameters of 0.014 inch and 0.018 inch (0.036 mm and 0.46 mm, respectively).

As can be seen in Table 1, standard guidewire diameters are 0.014 inch, 0.018 inch, and 0.035 inch for most coronary and peripheral vessel applications. While other guidewire diameters are contemplated, these diameters comprise the vast majority of commercially available guidewires. Table 1 shows the ranges of diameters for a drawn filled tubing guidewire including nominal diameters and preferred diameters for the disclosed invention.

TABLE 1

| | (inches) | | | | | | | |
|---|---|---|---|---|---|---|---|---|
| Standard Guidewire Diameters | Overall DFT Wire Diameters | | Preferred Overall DFT | | Nitinol Core Diameters | | Preferred Nitinol Core Diameters | |
| A | B | C | D | E | F | G | H | I |
| 0.014 | 0.013 | 0.014 | 0.0132 | 0.0135 | 0.0092 | 0.0128 | 0.0094 | 0.0125 |
| 0.018 | 0.0165 | 0.018 | 0.017 | 0.0175 | 0.0142 | 0.0148 | 0.0143 | 0.0145 |
| 0.035 | 0.029 | 0.035 | 0.028 | 0.032 | 0.025 | 0.03 | 0.026 | 0.029 |

TABLE 2

| (inches) Double Wall Thickness | | | | | |
|---|---|---|---|---|---|
| D-F | D-H | E-G | E-I | Wall Thickness | Wall Thickness average/2 |
| 0.004 | 0.0038 | 0.0007 | 0.001 | 0.0025 | 0.0012 |
| 0.0028 | 0.0027 | 0.0027 | 0.003 | 0.0029 | 0.0015 |
| 0.003 | 0.002 | 0.002 | 0.003 | 0.0035 | 0.0018 |

Referring to Table 1, a standard guidewire diameter for a DFT wire of 0.014 inch (column A) can range from 0.013 inch to 0.014 inch, as shown in columns B and C respectively. A preferred overall diameter DFT wire for the 0.014 inch wire (column A) can range from 0.0132 inch to 0.0135 inch, as shown in columns D and E respectively. The nominal nitinol core diameter range is shown in columns F and G, and the preferred nitinol core diameter range is shown in columns H and I. From Table 1, one can determine the overall diameter range for each of the three standard guidewires listed in column A, as well as the diameter ranges of the nitinol core wire.

The wall thickness of the outer layer 20 is derived from the dimensions set forth in Table 1. Referring to Table 2, by subtracting the preferred overall diameter of the DFT wire in column D from the nitinol core diameter in column F (0.0132 inch–0.0092 inch=0.004 inch), the wall thickness of the outer layer 20 is derived, as shown in column D-F. Since there are two wall thicknesses in the diameter dimension, the "average" wall thickness column in Table 2 is divided by two to obtain the wall thickness of the outer layer. For example, the preferred wall thickness for a 0.014 inch diameter guidewire is calculated by subtracting D (0.0132) from H (0.0094) to equal $$\frac{0.0038 \text{ inch}}{2}$$

to equal 0.0019 inch wall thickness. The column headed "average" is calculated by the formula $$\frac{(D-H)+(E-I)}{2},$$

which is the total average wall thickness of the outer layer. The average wall thickness of a single layer of the outer layer is calculated in the column headed "average/2" and is calculated using the formula $$\frac{(D-H)+(E-I)}{2} \div 2.$$

For example, in one embodiment, a 0.014 inch diameter DFT guidewire has an "average/2" outer layer single wall thickness 21 of 0.0012 inch $$\frac{(D-H)-(E-I)}{2} \div 2.$$

In another embodiment, a 0.018 inch diameter DFT guidewire has an "average/2" outer layer single wall thickness 21 of 0.0015 inch. In another embodiment, a 0.035 inch diameter DFT guidewire has an "average/2" outer layer single wall thickness 21 of 0.0018 inch.

Figure 7:
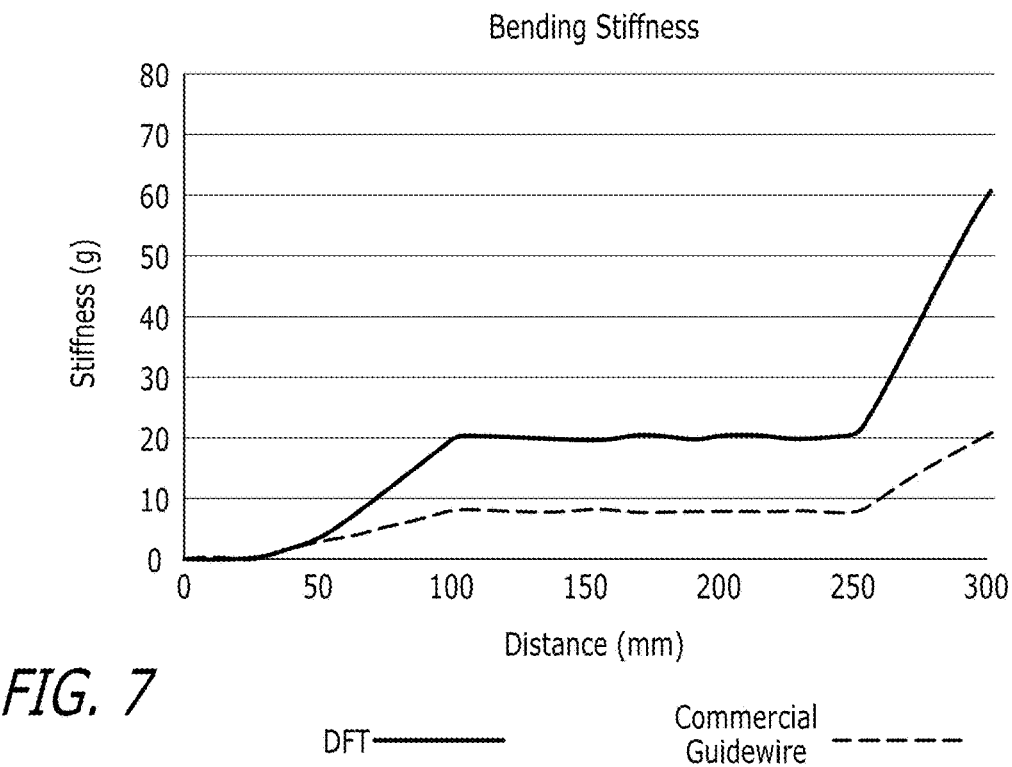
FIG. 7 is a graph depicting the bending stiffness of a drawn filled tubing guidewire of the invention compared to a commercially available guidewire.
Figure 8:
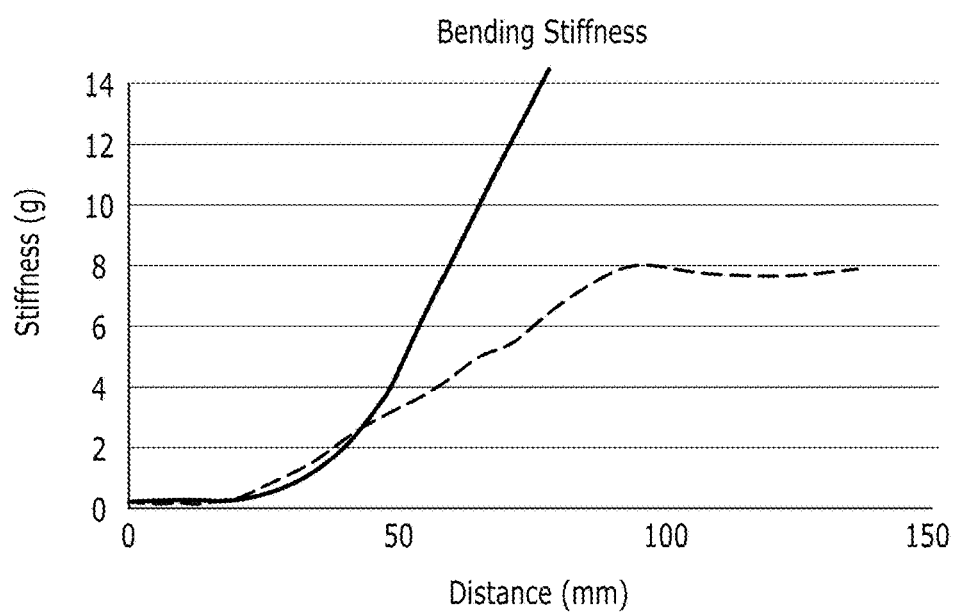
FIG. 8 is a graph depicting the bending stiffness of a drawn filled tubing guidewire of the invention compared to a commercially available guidewire.

The guidewire 10 disclosed herein is formed from drawn filled tubing (DFT) and after processing as disclosed herein, including forming a feather edged joint 30, has bending stiffness characteristics similar or superior to commercially available guidewires. As shown in the graphs of FIGS. 7 and 8, the bending stiffness of a DFT guidewire 10 is compared to that of a commercially available guidewire manufactured and sold by Abbott Cardiovascular Systems, Inc., Santa Clara, California. The bending stiffness from the distal tip of each guidewire to about 50 mm is similar and shows a high degree of flexibility due to a very low bending stiffness. From about 50 mm to about 150 mm, the DFT guidewire 10 has a higher bending stiffness than the commercial guidewire, which means that DFT guidewire 10 has better pushability and torque response than the commercial guidewire.

Figure 9:
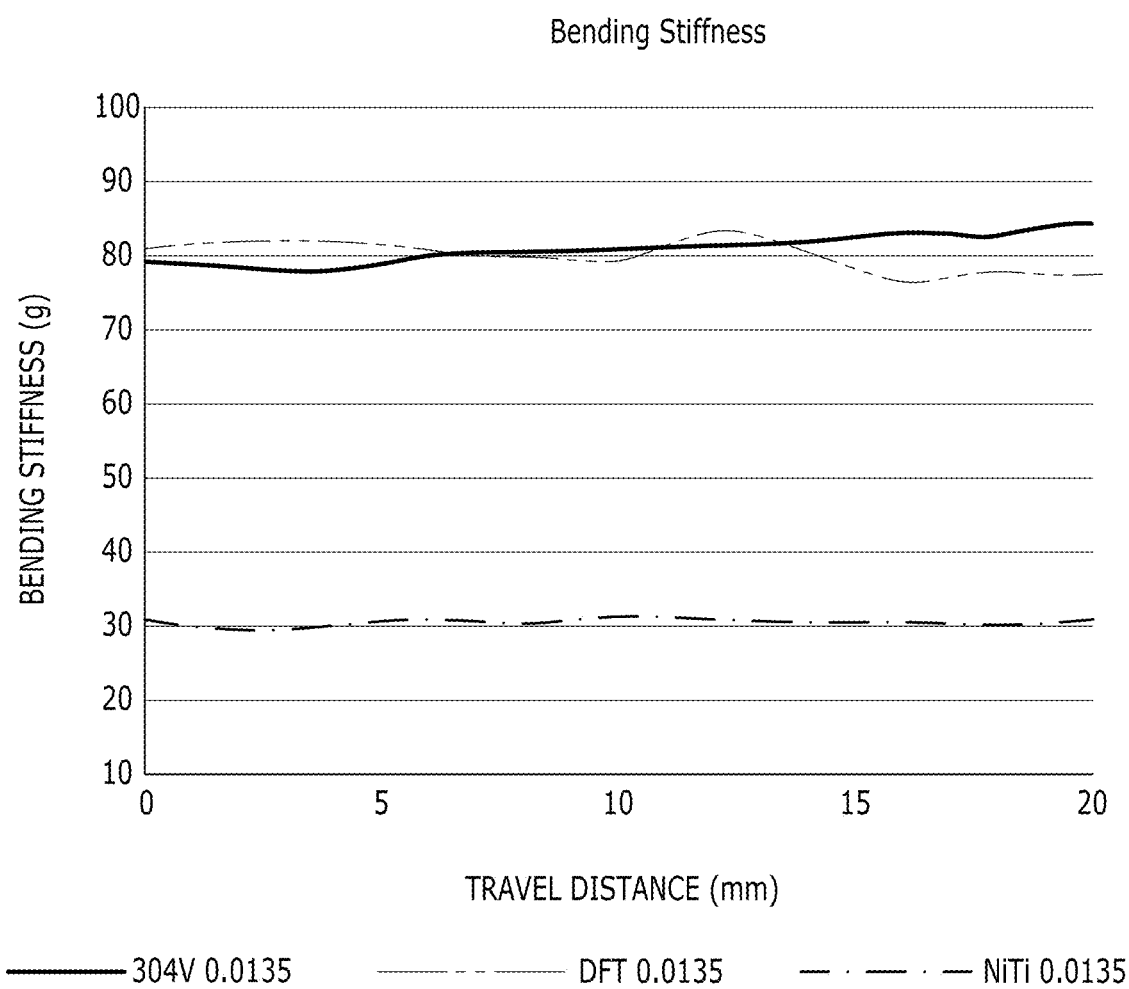
FIG. 9 is a graph depicting the bending stiffness constant diameter wires including of a drawn filled tubing guidewire of the invention compared to a commercially available guidewire.

Referring to the graph in FIG. 9, the bending stiffness of a constant diameter guidewire of 0.0135 inch was compared among a superelastic nitinol guidewire, a 304V stainless steel guidewire, and a DFT guidewire. As can be seen in FIG. 9, the superelastic nitinol guidewire has a low and relatively constant bending stiffness. The DFT guidewire and the 304V stainless steel guidewire have similar high and relatively constant bending stiffness. Thus, comparing the graphs from FIGS. 7 and 8 to FIG. 9, it can be seen that once the DFT guidewire 10 has the distal portion of the outer layer removed and the multiple tapers formed in the distal portion, the DFT guidewire performs as well or better than the commercially available guidewires.

Figure 10:
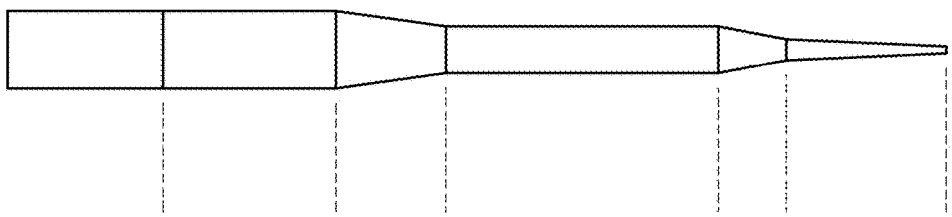
FIG. 10 is an elevational view of a prior art guidewire depicting a distal section having multiple tapered sections.

The bending stiffness of the drawn filled tubing (DFT) disclosed herein can also be altered by applying a parabolic grind along the nitinol distal section of the guidewire. A parabolic grind profile was described in commonly owned and commonly assigned U.S. Ser. No. 16/671,044 filed Oct. 31, 2019, the entire contents of which are incorporated herein by reference. Rather than grinding the nitinol inner core member 18 as shown in FIG. 6 with a first tapered section 38 and a second tapered section 44, a parabolic grind can be applied instead. Thus, referring to FIGS. 31-33 of U.S. Ser. No. 16/671,044, now renumbered as FIGS. 10-12 herein, the distal section of the guidewire is reduced in cross-section to be more flexible when navigating tortuous vessels, such as coronary arteries. The distal section of the guidewire must be both flexible and pushable, that is the distal section must flex and be steerable through the tortuous arteries, and also have some stiffness so that it can be pushed or advanced through the arteries without bending or kinking. A prior art guidewire is shown in FIG. 10 and has a distal section comprised of tapered sections and core sections with no taper. The resulting bending stiffness is shown in the graph in FIG. 12 wherein the bending stiffness decreases at each tapered position, and the bending stiffness remains constant along the core section that is not tapered. The tapered distal section of the prior art guidewire of FIG. 10 provides abrupt changes in bending stiffness that can reduce the tactile feel to the physician when advancing the guidewire through tortuous anatomy. In fact, in some prior art guidewires, the abrupt change in bending stiffness can result in the distal tip of the guidewire to kink or prolapse into a side branch vessel. Prolapse can be dangerous to the patient in that the artery can be damaged or punctured. Importantly, it is preferred to maintain the outer diameter of the core section as far distal as possible to maintain torque. Each tapered section loses torque, which is critical in advancing the guidewire through tortuous vessels.

Figure 11:
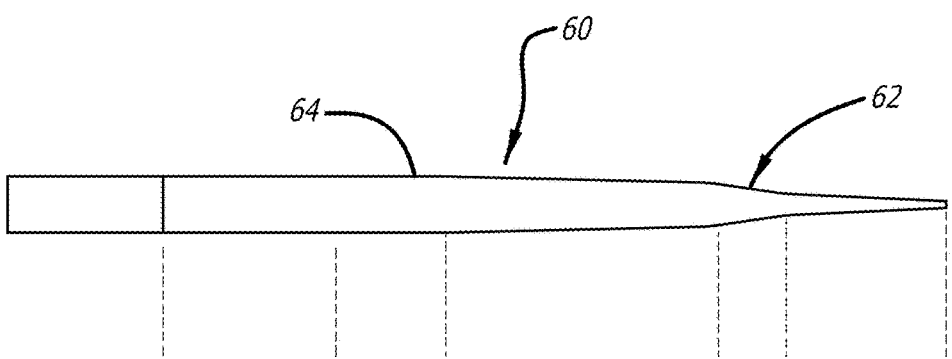
FIG. 11 is an elevational view of a guidewire depicting a distal section having a parabolic grind profile.
Figure 12:
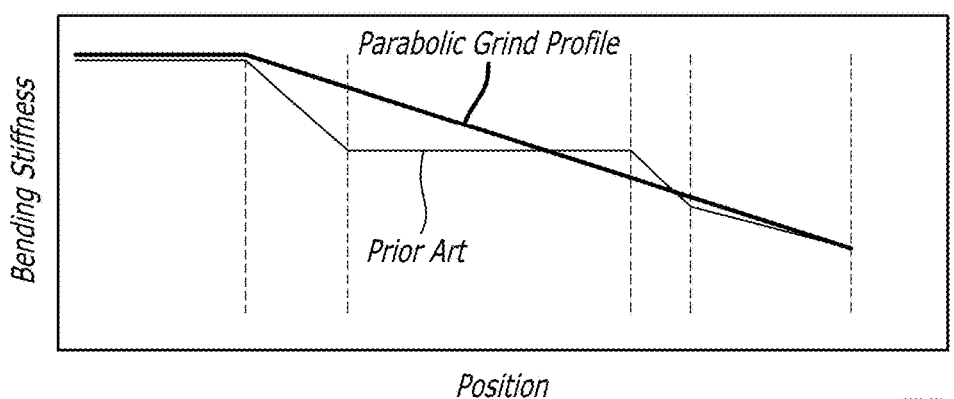
FIG. 12 is a graph depicting the bending stiffness along the distal section of the guidewires shown in FIGS. 10 and 11.
Figure 13:
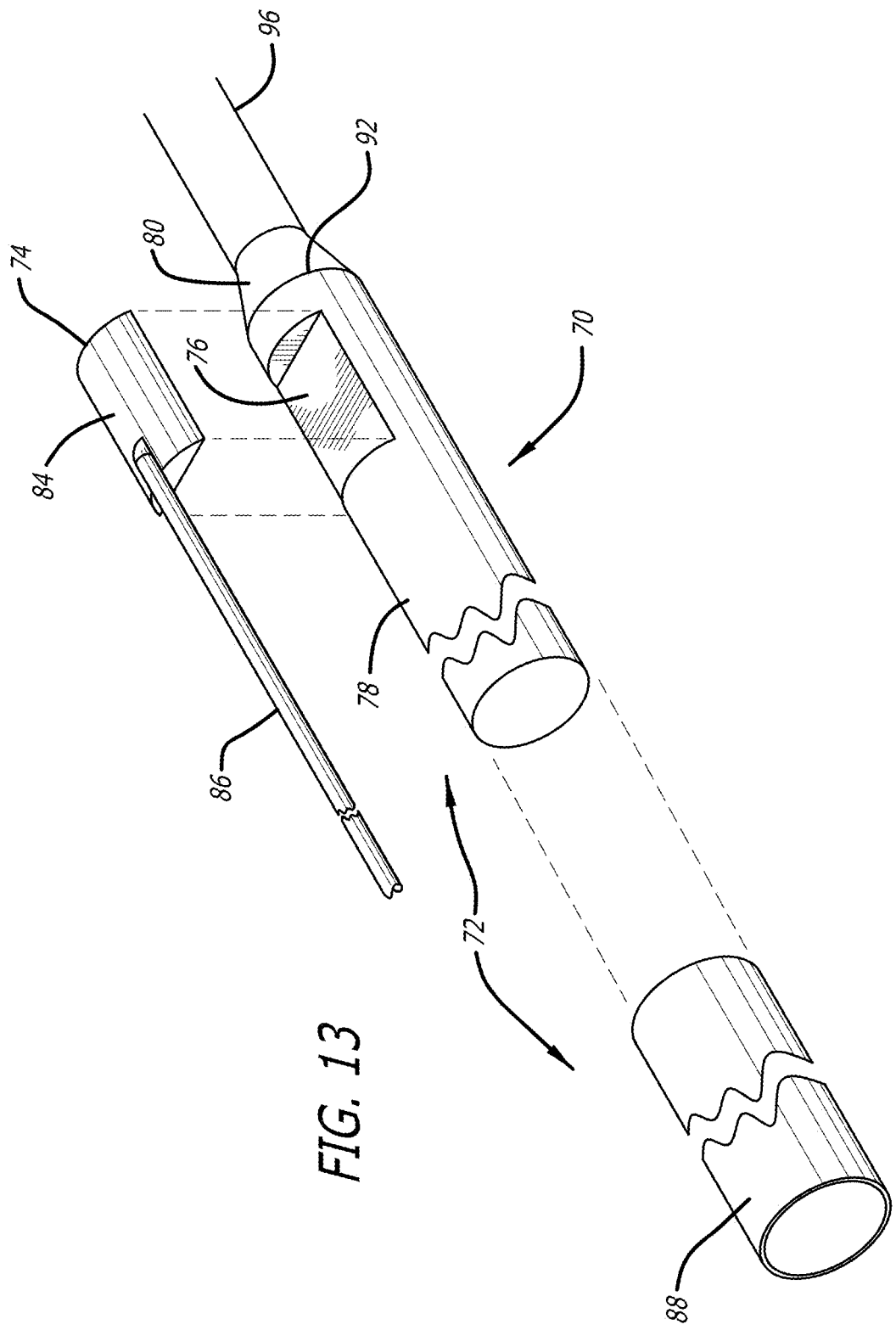
FIG. 13 is a perspective view of a drawn filled tubing guidewire depicting a pressure sensor and sensor pocket.

In keeping with the invention, a parabolic distal section 62 of a guidewire 60 is shown in FIG. 11 wherein a significant portion of the distal section has been ground to form a continuous taper. More specifically, the continuous taper is formed by a parabolic grind along parabolic distal section 62 of the guidewire 60. The parabolic grind provides a smooth curvilinear transition along section 62 that is highly flexible and yet maintains a linear change in stiffness as shown in the graph of FIG. 12. Not only is parabolic distal section 62 flexible, but it has a linear change in stiffness thereby providing excellent torque and tactile feedback to the physician when advancing the guidewire through tortuous anatomy. A tapered section 64 that is not curvilinear (not a parabolic grind section) is located on the guidewire 60 distal of the parabolic distal section 62 and it provides reduced bending stiffness and a linear change in bending stiffness as shown in the graph of FIG. 12. It is intended that the parabolic grind profile be applied to only the nitinol inner core member along the parabolic distal section 62.

Bending stiffness can be measured in a variety of ways. Typical methods of measuring bending stiffness include extending a portion of the sample to be tested from a fixed block with the sample immovably secured to the fixed block and measuring the amount of force necessary to deflect the end of the sample that is away from the fixed block a predetermined distance. A similar approach can be used by fixing two points along the length of a sample and measuring the force required to deflect the middle of the sample a fixed amount. Those skilled in the art will realize that a large number of variations on these basic methods exist including measuring the amount of deflection that results from a fixed amount of force on the free end of a sample, and the like. Other methods of measuring bending stiffness may produce values in different units of different overall magnitude, however, it is believed that the overall shape of the graph will remain the same regardless of the method used to measure bending stiffness.

The embodiments of the drawn filled tubing (DFT) guidewire disclosed herein are particularly suitable for use in conjunction with a pressure sensor. During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis. A number of pressure sensing devices, however, may pose technical challenges for steering, tracking, torqueing or otherwise navigating the device within the vasculature. For example, medical devices may include a relatively stiff pressure sensor located at or near the distal tip of the device and/or a sensor housing (in which the sensor is mounted) that may also be relatively stiff. Disclosed herein are a number of medical device that include pressure sensing capabilities and may be more easily steered, tracked, torqued, and/or otherwise navigated through the anatomy. The DFT guidewire of the present invention is used to carry a pressure sensor through the coronary and peripheral vessels to measure blood pressure and possibly FFR, as well as other measurements.

In one embodiment, shown in FIGS. 13-16B, a drawn filled tubing (DFT) guidewire 70 is processed according to the embodiment shown in FIGS. 1-6. The difference, however, is in this embodiment the proximal section 72 is adapted to carry a pressure sensor 74 (or any other type of measuring device). The pressure sensor 74 can be any sensor known in the art and may include a semiconductor (e.g., silicon wafer) pressure sensor, piezoelectric pressure sensor, a fiber optic or optical pressure sensor, a Fabry-Perot type sensor, an ultrasound transducer and/or ultrasound pressure sensor, a magnetic pressure sensor, a solid-state pressure sensor, and the like. In this embodiment, a sensor pocket 76 is formed in the proximal section 72 of the drawn filled tubing 70 for mounting the pressure sensor 74. The sensor pocket 76 can be formed by grinding the outer surface 78 of DFT guidewire 70 to a depth and shape that is configured to receive the pressure sensor 74 without compromising the integrity of the DFT guidewire 70. Also, it is preferred that the pressure sensor 74 be configured so as to not disrupt blood flow or impede the movement of the DFT guidewire 70 through the vasculature. Preferably, the sensor pocket 76 is positioned on the DFT guidewire 70 just proximal of the tapered transition segment 80 where the outer layer 82 is first ground down to form the tapered transition segment 80. The grinding procedure for forming the sensor pocket 76 can be performed by any method well known in the prior art.

Figure 15:
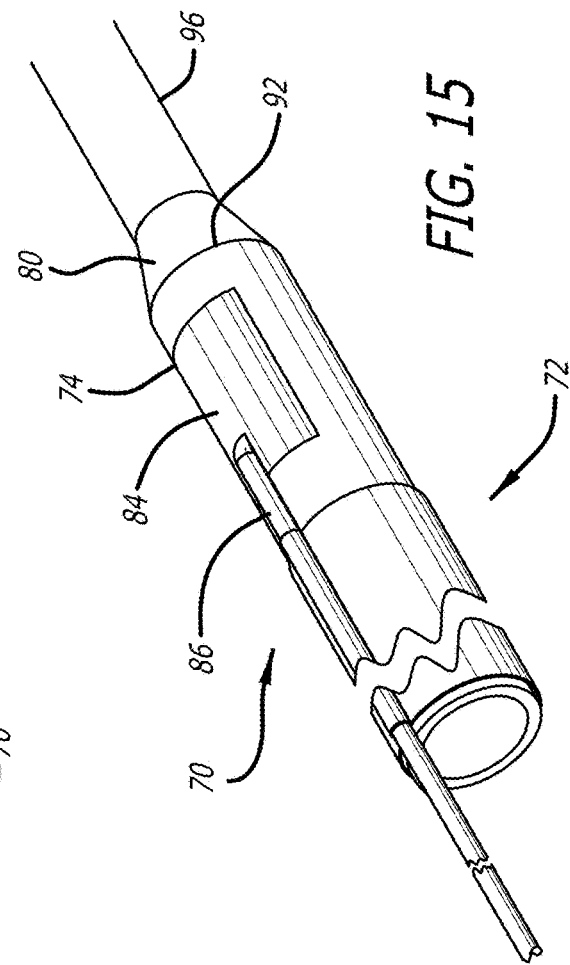
FIG. 15 is a partial perspective view of the guidewire shown in FIG. 13 depicting the pressure sensor attached to the sensor pocket.

Pressure sensors 74 are well known in the art and can take many different sizes and shapes. As shown in FIG. 15, for example, the pressure sensor 74 has a contoured outer surface 84 to conform to the curved outer surface 78 of the DFT guidewire 70 so that there are no sharp edges that could cause injury to the vasculature. The pressure sensor 74 can be attached to the sensor pocket 76 by any known means including adhesive, laser welding, soldering, brazing, and the like.

In further reference to FIGS. 13-16B, a power and data transmission cable 86 is attached to the pressure sensor 74 and the cable 86 extends proximally along the outer surface 78 of the DFT guidewire 70 to a location outside of the patient so that it can be attached to the appropriate monitoring equipment. A polymer sleeve 88 is formed over the cable 86 and at least a portion of the outer surface 78 of the DFT guidewire 70 in order to protect the cable 86 and prevent it from interfering with the movement of the guidewire in the vasculature. While a polymer sleeve 88 is preferred, other covers are contemplated such as polymer bands, radiopaque marker bands, braided materials, and the like.

It is preferred that the sensor pocket 76 and the attached pressure sensor 74 be positioned very close to the tapered transition segment 80, but proximal thereto. In one embodiment, a distal edge 90 of the sensor pocket 76 is a length 94 between 0.1 mm and 30.0 mm from a first point 92 which marks the beginning of the tapered transition segment 80. In another embodiment, the length 94 is between 0.1 mm and 10.0 mm.

Figure 14:
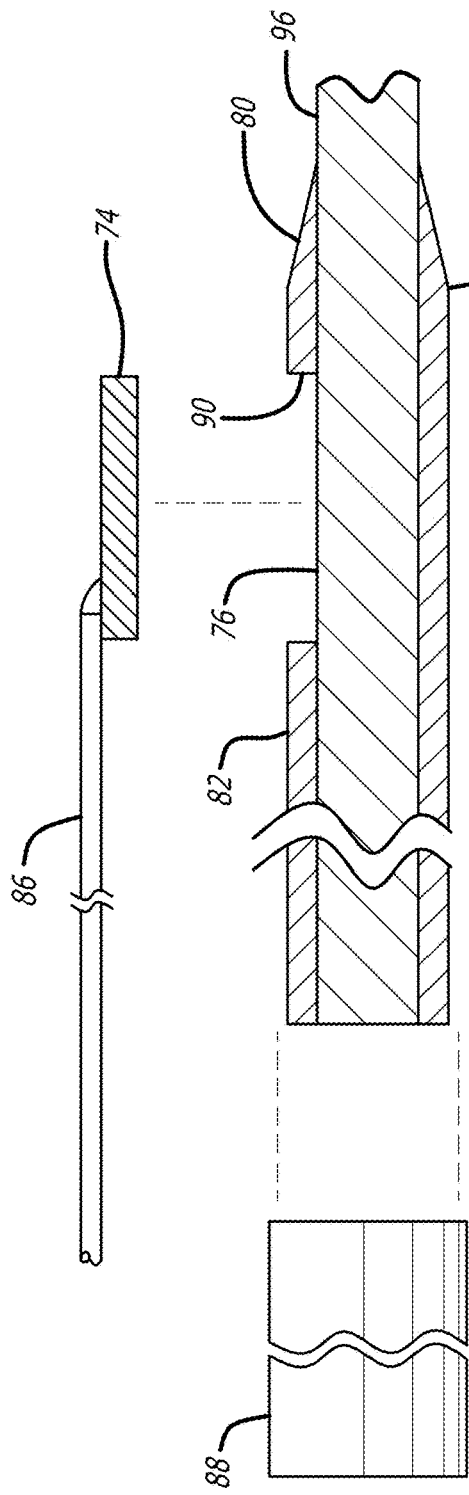
FIG. 14 is a longitudinal cross-sectional view of the drawn filled tubing guidewire of FIG. 13.

Referring to FIG. 14, the depth of the sensor pocket 76 is shown to be equal to the thickness of the outer layer 82. Depending on the thickness of the pressure sensor 74, the depth of the sensor pocket 76 can be more or less than depicted in FIG. 14, and extends into an inner core member 96 which is formed from nitinol as previously described. It is preferred that the depth of the sensor pocket 76 into the inner core member be minimal, however, it is possible that the sensor pocket 76 extends half way through the diameter of the DFT guidewire 70, which means the pocket would extend well into the nitinol inner core member 96.

Guidewires like the ones disclosed herein typically will have one or more coils attached to the distal end as well as a solder structure, neither of which are shown. Further, the drawn filled tubing is manufactured by know means and need not be further described. The multiple distal tapers are formed by centerless grinding machines and the method of grinding is well known and need not be further described.

With respect to the embodiment shown in FIGS. 13-16B, the DFT guidewire 70 has an inner core member 96 extending the entire length of the guidewire 70. In some embodiments, it is preferred that the inner core member 96 extend only in a distal portion of the guidewire so that the outer layer 82 covers only a short length of the proximal end of the inner core member 96. In one embodiment, the outer layer 82 overlaps and covers less than 2.5 cm of the proximal end of the inner core member 96.

While the present invention has been described and illustrated in terms of its use as an intravascular guidewire, it will be apparent to those skilled in the art that the present invention can be applied to other medical devices. Moreover, modifications and improvements may be made to the above-described exemplary embodiments without departing from the scope of the invention.

We claim:

1. A guidewire, comprising:
an elongated tubular member having a proximal end and distal end;
the elongated tubular member having an inner core member formed from a first metal alloy and an outer layer formed from a second metal alloy surrounding at least a portion of the inner core member; and
a feather edged joint formed only on the outer layer and defining a tapered transition segment between the outer layer and the inner core member wherein the feather edged joint extends radially outwardly along a first constant diameter section of the inner core member.

2. The guidewire of claim 1, wherein the first metal alloy is formed from a linear elastic alloy or a superelastic alloy.

3. The guidewire of claim 2, wherein the linear elastic alloy of the first metal alloy is selected from the group of metal alloys consisting of NiTi, CuNiTi and NiTiCr.

4. The guidewire of claim 3, wherein the second metal alloy is selected from the group of metal alloys consisting of 35N LT, L605, MP35, MP35N, cobalt-chromium, titanium, NiTiCo, NiTiCr, and NiTi ternary alloys.

5. The guidewire of claim 4, wherein the inner core member is a solid wire.

6. The guidewire of claim 5, wherein the inner core member has a nominal diameter at an untapered section in the range of 0.0094 inch to 0.029 inch.

7. The guidewire of claim 6, wherein the outer layer has a nominal transverse single wall thickness at an untapered section in the range of 0.0012 inch to 0.0018 inch.

8. The guidewire of claim 1, wherein the tapered transition segment of the feather edged joint extends a length along the elongated tubular member beginning at a first point where an average transverse single wall thickness of the outer layer is a constant, and ends at a second point where the average transverse single wall thickness of the outer layer is zero.

9. The guidewire of claim 8, wherein the outer layer tapers distally from the first point to the second point to form the feather edged joint.

10. The guidewire of claim 9, wherein the first constant diameter section of the inner core member extends distally from the second point to a third point.

11. The guidewire of claim 10, wherein the inner core member has a first tapered section extending from the third point to a fourth point.

12. The guidewire of claim 11, wherein the inner core member has a second constant diameter section extending from the fourth point to a fifth point.

13. The guidewire of claim 12, wherein the inner core member has a second tapered section extending from the fifth point to a sixth point.

14. The guidewire of claim 13, wherein the inner core member has a third constant diameter section extending from the sixth point to the distal end of the elongated member.

15. The guidewire of claim 14, wherein the third constant diameter section has a nominal diameter in the range from 0.002 inch to 0.0060 inch, and the third constant diameter section is less than the first constant diameter section and the second constant diameter section.

16. The guidewire of claim 15, wherein no portion of the outer layer surrounds the inner core member from the second point to the distal end of the elongated tubular member.

17. The guidewire of claim 16, wherein the first tapered segment has a length in the range from 2.0 cm to 6.0 cm.

18. The guidewire of claim 17, wherein the second tapered segment has a length in the range from 2.0 cm to 12.0 cm.

19. The guidewire of claim 18, wherein an angle of the first tapered segment and the second tapered segment is in the range from 0.1° to 2.0°.

20. The guidewire of claim 1, wherein the inner core member has a diameter at an untapered section, for a 0.014 inch guidewire, in the range from 0.0094 inch to 0.0125 inch.

21. The guidewire of claim 1, wherein the inner core member has a diameter at an untapered section, for a 0.018 inch guidewire, in the range from 0.0143 inch to 0.0145 inch.

22. The guidewire of claim 1, wherein the inner core member has a diameter at an untapered section, for a 0.035 inch guidewire, in the range from 0.0260 inch to 0.0290 inch.

23. The guidewire of claim 1, wherein a diameter of the inner core member at an untapered section, for a 0.014 inch guidewire, is no more than 93.0% of an overall diameter of the elongated tubular member.

24. The guidewire of claim 1, wherein a diameter of the inner core member at an untapered section, for a 0.018 inch guidewire, is no more than 82.0% of an overall diameter of the elongated tubular member.

25. The guidewire of claim 1, wherein a diameter of the inner core member at an untapered section, for a 0.035 inch guidewire, is no more than 91.0% of an overall diameter of the elongated tubular member.

26. The guidewire of claim 1, wherein the outer layer has a transverse single wall thickness at an untapered section, for a 0.014 inch guidewire, of 0.0012 inch.

27. The guidewire of claim 1, wherein the outer layer has a transverse single wall thickness at an untapered section, for a 0.018 inch guidewire, of 0.0015 inch.

28. The guidewire of claim 1, wherein the outer layer has a transverse single wall thickness at an untapered section, for a 0.035 inch guidewire, of 0.0018 inch.

29. The guidewire of claim 1, wherein a wall thickness of the outer layer at an untapered section, for a 0.014 inch guidewire, is no more than 14.0% of an overall diameter of the elongated tubular member.

30. The guidewire of claim 1, wherein a wall thickness of the outer layer at an untapered section, for a 0.018 inch guidewire, is no more than 9.0% of an overall diameter of the elongated tubular member.

31. The guidewire of claim 1, wherein a wall thickness of the outer layer at an untapered section, for a 0.035 inch guidewire, is no more than 4.0% of an overall diameter of the elongated tubular member.

32. A guidewire, comprising:
an elongated drawn filled tube having a proximal end and distal end;
the elongated drawn filled tube having an inner core member formed from a first metal alloy and an outer layer formed from a second metal alloy surrounding at least a portion of the inner core member; and
a feather edged joint formed only on the outer layer and defining a tapered transition segment between the outer layer and the inner core member wherein the feather edged joint extends radially outwardly along a first constant diameter section of the inner core member.

33. The guidewire of claim 32, wherein the first metal alloy is formed from a linear elastic alloy.

34. The guidewire of claim 33, wherein the linear elastic alloy of the first metal alloy is selected from the group of metal alloys consisting of NiTi, CuNiTi and NiTiCr.

35. The guidewire of claim 34, wherein the second metal alloy is selected from the group of metal alloys consisting of 35N LT, L605, MP35, MP35N, cobalt-chromium, titanium, NiTiCo, NiTiCr and NiTi ternary alloys.

36. The guidewire of claim 35, wherein the inner core member is a solid wire.

37. The guidewire of claim 36, wherein the inner core member has a nominal diameter at an untapered section in the range of 0.0094 inch to 0.029 inch.

38. The guidewire of claim 37, wherein the outer layer has a nominal transverse single wall thickness at an untapered section in the range of 0.0012 inch to 0.0018 inch.

39. The guidewire of claim 32, wherein the tapered transition segment of the feather edged joint extends a length along the elongated drawn filled tube beginning at a first point where an average transverse single wall thickness of the outer layer is a constant, and ends at a second point where the average transverse single wall thickness of the outer layer is zero.

40. The guidewire of claim 39, wherein the outer layer tapers distally from the first point to the second point to form feather edged joint.

41. The guidewire of claim 40, wherein the first constant diameter section of the inner core member extends distally from the second point to a third point.

42. The guidewire of claim 41, wherein the inner core member has a first tapered section extending from the third point to a fourth point.

43. The guidewire of claim 42, wherein the inner core member has a second constant diameter section extending from the fourth point to a fifth point.

44. The guidewire of claim 43, wherein the inner core member has a second tapered section extending from the fifth point to a sixth point.

45. The guidewire of claim 44, wherein the inner core member has a third constant diameter section extending from the sixth point to the distal end of the elongated member.

46. The guidewire of claim 45, wherein the third constant diameter section has a nominal diameter in the range from 0.002 inch to 0.0060 inch, and the third constant diameter section is less than the first constant diameter section and the second constant diameter section.

47. The guidewire of claim 46, wherein no portion of the outer layer surrounds the inner core member from the second point to the distal end of the elongated tubular member.

48. The guidewire of claim 47, wherein the first tapered segment has a length in the range from 2.0 cm to 6.0 cm.

49. The guidewire of claim 48, wherein the second tapered segment has a length in the range from 2.0 cm to 12.0 cm.

50. The guidewire of claim 49, wherein an angle of the first tapered segment and the second tapered segment is in the range from 0.1° to 2.0°.

51. The guidewire of claim 32, wherein the inner core member has a diameter at an untapered section, for a 0.014 inch guidewire, in the range from 0.0094 inch to 0.0125 inch.

52. The guidewire of claim 32, wherein the inner core member has a diameter at an untapered section, for a 0.018 inch guidewire, in the range from 0.0143 inch to 0.0145 inch.

53. The guidewire of claim 32, wherein the inner core member has a diameter at an untapered section, for a 0.035 inch guidewire, in the range from 0.0260 inch to 0.0290 inch.

54. The guidewire of claim 32, wherein a diameter of the inner core member at an untapered section, for a 0.014 inch guidewire is no more than 93.0% of an overall diameter of the elongated tubular member.

55. The guidewire of claim 32, wherein a diameter of the inner core member at an untapered section, for a 0.018 inch guidewire, is no more than 82.0% of an overall diameter of the elongated tubular member.

56. The guidewire of claim 32, wherein a diameter of the inner core member at an untapered section, for a 0.035 inch guidewire, is no more than 91.0% of an overall diameter of the elongated tubular member.

57. The guidewire of claim 32, wherein the outer layer has a preferred transverse single wall thickness at an untapered section, for a 0.014 inch guidewire, of 0.0012 inch.

58. The guidewire of claim 32, wherein the outer layer has a preferred transverse single wall thickness at an untapered section, for a 0.018 inch guidewire, of 0.0015 inch.

59. The guidewire of claim 32, wherein the outer layer has a preferred transverse single wall thickness at an untapered section, for a 0.035 inch guidewire, of 0.0018 inch.

60. The guidewire of claim 32, wherein a wall thickness of the outer layer at an untapered section, for a 0.014 inch guidewire, is no more than 14.0% of an overall diameter of the elongated tubular member.

61. The guidewire of claim 32, wherein a wall thickness of the outer layer at an untapered section, for a 0.018 inch guidewire, is no more than 9.0% of an overall diameter of the elongated tubular member.

62. The guidewire of claim 32, wherein a wall thickness of the outer layer at an untapered section, for a 0.035 inch guidewire, is no more than 4.0% of an overall diameter of the elongated tubular member.

\* \* \* \* \*